(12) United States Patent
Jackson et al.

(10) Patent No.: US 11,198,664 B2
(45) Date of Patent: Dec. 14, 2021

(54) PROCESS FOR THE PURIFICATION OF ETHYLENE GLYCOL

(71) Applicant: JOHNSON MATTHEY DAVY TECHNOLOGIES LIMITED, London (GB)

(72) Inventors: Simon Jackson, Billingham (GB); Adam Armour Snaith, Billingham (GB); Michael William Marshall Tuck, Billingham (GB); David John Watson, Stockton-on-Tees (GB); Michael Anthony Wood, Stockton-on-Tees (GB)

(73) Assignee: Johnson Matthey Davy Technologies Limited, London (GB)

( * ) Notice: Subject to any disclaimer, the term of this patent is extended or adjusted under 35 U.S.C. 154(b) by 0 days.

(21) Appl. No.: 16/625,015

(22) PCT Filed: Jun. 26, 2018

(86) PCT No.: PCT/GB2018/051775
§ 371 (c)(1),
(2) Date: Dec. 20, 2019

(87) PCT Pub. No.: WO2019/002839
PCT Pub. Date: Jan. 3, 2019

(65) Prior Publication Data
US 2020/0216377 A1    Jul. 9, 2020

(30) Foreign Application Priority Data

Jun. 30, 2017   (GB) ..................................... 1710508

(51) Int. Cl.
*C07C 29/84*   (2006.01)
(52) U.S. Cl.
CPC .................................. *C07C 29/84* (2013.01)
(58) Field of Classification Search
CPC .......... C07C 29/80; C07C 29/82; C07C 29/84
See application file for complete search history.

(56) References Cited

U.S. PATENT DOCUMENTS

| | | | | |
|---|---|---|---|---|
| 3,875,019 A * | 4/1975 | Cocuzza | .............. | B01D 53/263 203/18 |
| 4,087,470 A * | 5/1978 | Suzuki | .................. | C07C 29/149 568/864 |
| 4,113,662 A * | 9/1978 | Wall | ........................ | B01J 23/80 502/329 |
| 4,349,417 A * | 9/1982 | Rebsdat | ................ | C07C 29/106 203/33 |
| 6,437,199 B1* | 8/2002 | Oka | ...................... | C07C 29/106 568/866 |
| 6,514,388 B1 | 2/2003 | Adrian et al. | | |
| 8,002,953 B2* | 8/2011 | Lee | ....................... | B01D 3/002 203/19 |
| 8,063,255 B2* | 11/2011 | Slapak | ..................... | C07C 29/12 568/868 |
| 8,143,458 B2* | 3/2012 | Kalagias | .................. | C07C 29/82 568/854 |
| 10,266,470 B2* | 4/2019 | Huizenga | ................. | C07C 29/82 |
| 10,538,476 B2* | 1/2020 | Hiles | ....................... | B01D 3/346 |
| 2009/0270656 A1* | 10/2009 | Fukuoka | ................ | B01D 3/009 568/852 |
| 2010/0094065 A1* | 4/2010 | Slapak | .................... | C07C 29/80 568/860 |
| 2011/0282107 A1* | 11/2011 | Maurer | .................... | C07C 29/60 568/868 |

(Continued)

FOREIGN PATENT DOCUMENTS

| CN | 105085165 A | * 11/2015 |
|---|---|---|
| CN | 105085165 A | 11/2015 |

(Continued)

OTHER PUBLICATIONS

C. Cui et al., Industrial & Engineering Chemistry Research, 5078-5091 (2017) (Year: 2017).*
W. Luyben, 168 Separation and Purification Technology, 62-67 (2016) (Year: 2016).*
A. Kumar et al., 45 AIChE Journal, 51-68 (1999) (Year: 1999).*
S. Rebsdat et al. 13 Ulmann's Encyclopedia of Industrial Chemistry, 531-546 (2012) (Year: 2012).*

(Continued)

*Primary Examiner* — Alexander R Pagano
(74) *Attorney, Agent, or Firm* — BakerHostetler (57) ABSTRACT

The present invention is directed to a process for the purification of ethylene glycol from a crude stream thereof. The process comprises passing the stream of crude ethylene glycol to a first distillation column in which light compounds within the crude stream are separated overhead and a lights-removed crude ethylene glycol stream is removed from at or near the bottom of the first distillation column; passing the lights-removed crude ethylene glycol stream removed from at or near the bottom of the first distillation column to a second distillation column in which purified ethylene glycol is separated and recovered from heavy components present in the lights-removed crude ethylene glycol stream; removing a stream from at or near the bottom of the second distillation column which comprises residual ethylene glycol together with diethylene glycol and heavy compounds and passing said stream to a third distillation column in which the heavy compounds are separated from the stream comprising ethylene glycol and diethylene glycol; and removing the stream comprising ethylene glycol and diethylene glycol from the third distillation column and passing said stream to a fourth distillation column in which the ethylene glycol is separated from the diethylene glycol.

17 Claims, 1 Drawing Sheet

(56) References Cited

U.S. PATENT DOCUMENTS

| | | | | |
|---|---|---|---|---|
| 2012/0136178 A1* | 5/2012 | Smaardijk | ............... | C07C 29/64 |
| | | | | 568/867 |
| 2012/0184783 A1* | 7/2012 | Barnicki | .............. | B01J 31/2409 |
| | | | | 568/868 |
| 2013/0284584 A1* | 10/2013 | Xiao | ........................ | C07C 29/82 |
| | | | | 203/68 |
| 2016/0102035 A1* | 4/2016 | Fischer | ................... | C07C 43/11 |
| | | | | 568/621 |
| 2017/0327445 A1* | 11/2017 | Yague | ...................... | B01J 37/06 |
| 2017/0327446 A1* | 11/2017 | Zhang | ................... | B01D 3/146 |

FOREIGN PATENT DOCUMENTS

| | | | |
|---|---|---|---|
| CN | 106146299 | A | 11/2016 |
| CN | 106866373 | A * | 6/2017 |
| CN | 107200678 | A * | 9/2017 |
| EP | 0310187 | A2 | 4/1989 |
| EP | 0310189 | A2 | 4/1989 |
| JP | 2003300917 | A | 10/2003 |
| WO | 2012122566 | A1 | 9/2012 |

OTHER PUBLICATIONS

English Language Machine Translation CN-106866373-A (Year: 2017).*

English Language Machine Translation CN-107200678-A (Year: 2017).*

English Language Machine Translation CN-105085165-A (Year: 2015).*

* cited by examiner

PROCESS FOR THE PURIFICATION OF ETHYLENE GLYCOL

CROSS-REFERENCE TO RELATED APPLICATIONS

This application is the National Stage of International Patent Application No. PCT/GB2018/051775, filed Jun. 26, 2018, which claims priority to Great Britain Patent Application No. 1710508.1 filed Jun. 30, 2017, the entire disclosures of both of which are incorporated herein by reference for any and all purposes.

The present invention relates to a process for the purification of ethylene glycol. More particularly, it relates to a process for the purification of ethylene glycol produced from glycolic acid via a glycolic acid ester. Still more particularly, it relates to the purification of ethylene glycol from glycolic acid which has been formed from formaldehyde and synthesis gas.

Ethylene glycol has two main uses, as a component in antifreeze compositions and as a precursor in the production of polyesters. In particular, it is used in the production of polyethylene terephthalate which itself has a variety of uses including in the production of plastic bottles. It will, therefore, be understood that a significant volume of ethylene glycol is produced each year.

Various routes for the production of ethylene glycol have been proposed. For example, it can be produced from ethylene via ethylene oxide. In one alternative proposal, the ethylene glycol can be produced by the esterification and subsequent hydrogenation of glycolic acid.

The glycolic acid used in the production of the ethylene glycol may be produced by a variety of routes. For example, it can be formed by fermentation processes such as those described in US 2012/0178136, US 2012/0315682 and WO 2007/141316 or by electrochemical processes such as that described in US 2014/027303. However, the majority of the glycolic acid produced commercially is obtained by hydrocarbonylation of formaldehyde.

The reaction to form glycolic acid by the carbonylation of formaldehyde with carbon monoxide using strong acid catalysts is well known. The basic process was first disclosed by DuPont in U.S. Pat. No. 2,152,852. The process was for the preparation of glycolic acid in the liquid phase by reacting formaldehyde, water and carbon monoxide in the presence of a homogeneous acid catalyst at temperatures between 50° C. and 350° C. and at a pressure between 5 and 1500 atma. Sulphuric acid, hydrochloric acid, phosphoric acid, boron fluoride, formic acid and glycolic acid are described as suitable catalysts.

DuPont went on to obtain further patents for the production of glycolic acid such as U.S. Pat. No. 2,285,444 which discloses a continuous process for the hydrogenation of glycolic acid to ethylene glycol and U.S. Pat. No. 2,443,482 which discloses a continuous process for formaldehyde carbonylation.

The process for producing ethylene glycol was commercialised and operated by DuPont until the late 1960's when this route to ethylene glycol became uncompetitive. The plant was then operated for the production of glycolic acid in which sulphuric acid was used as catalyst at a temperature of 200° C. and at a pressure of from 400 to 700 bar.

The processes described in these initial early cases suffered from numerous problems. These problems included those attributable to the need to work at very high pressure. In addition, the selectivity was poor. It was also necessary to contend with the highly corrosive reaction mixture and the difficulty of removing the homogeneous acid catalyst such as sulphuric acid from the reaction product.

Various proposals have been made to address some or all of these problems. For example, in U.S. Pat. No. 3,859,349 there is a proposal to address the problems associated with separating the sulphuric acid catalyst and suggests using ion exchange resins as an alternative to neutralisation with calcium carbonate, which had been the previous approach. However, the ion exchange resins have limited thermal stability in aqueous environments leading to the loss of acid groups.

Another proposal was that described in U.S. Pat. No. 4,431,486 in which azeotropic distillation of crude glycolic acid was proposed as a means of reducing the water content in the recycle to the carbonylation reactors thereby minimising byproduct formation and increasing the yield from the feed formaldehyde.

Another approach has been to look at alternative catalyst systems as a means of reducing reactor operating pressure. Hydrogen fluoride has been suggested as being a suitable catalyst in U.S. Pat. Nos. 3,911,003, 4,016,208, 4,087,470, 4,136,112 and 4,188,494. Processes which use hydrogen fluoride in place of sulphuric acid as catalyst are suggested to allow operating pressures of 1 to 275 bar.

A further alternative process is disclosed in U.S. Pat. No. 4,052,452 in which Cu(I) or Ag salts in concentrated sulfuric acid are suggested as a means of increasing the carbon monoxide solubility and it is suggested that this enables the operating pressure to be reduced to between 0.1 and 30 atma. Whilst this may address the operating pressure issues, such systems are extremely sensitive to poisoning by water and separation and recycle of the metallic catalyst is difficult.

In U.S. Pat. No. 6,376,723 it is proposed that the reaction should be conducted with an acid catalyst having a pKa value of less than −1 in the presence of a sulphone as a means of moderating the reaction conditions. There is also a suggestion that heterogeneous catalysts could be used.

U.S. Pat. No. 4,140,866 looks at the problems associated with removing the sulfuric acid catalyst from glycolic acid produced by formaldehyde carbonylation. The proposed solution is to first treat the reaction mixture with an alkali metal hydroxide to form the dissolved sulfate salt and this is then precipitated on esterification of the glycolic acid with ethylene dioxide and removal of water.

A widely adopted strategy for overcoming the problems associated with separating homogeneous catalysts from reaction mixtures is to replace the homogeneous catalysts with heterogeneous catalysts that can easily be mechanically separated. Several solid acid materials have been suggested as suitable catalysts for use in formaldehyde carbonylation reactions. These include sulfonic acid ion exchange resins, aluminosilicate zeolites, polyoxometalate salts and alkyl sulfonic acid polysiloxanes.

The use of solid insoluble particulate acidic catalysts having a hydrogen ion exchange capacity in excess of 0.1 milliequivalents per gram was first described in GB1499245. Sulfonic acid based ion exchange resins, acid clays and zeolites are listed as suitable catalysts for formaldehyde carbonylation. These include sulfonic acid ion exchange resins, aluminosilicate zeolites, polyoxometalate salts and alkyl sulfonic acid polysiloxanes.

An alternative process for the preparation of glycolic acid or its esters is disclosed in DE3133353C2. In this process, formaldehyde is reacted with carbon monoxide and water or an alcohol in an inert diluent in two reaction steps. In the first step, formaldehyde is reacted with carbon monoxide using an acidic, solid, insoluble, finely distributed catalyst at a ratio of hydrogen ion exchange capacity of the catalyst to the molar amount of the formaldehyde of 1:1 to 5:1, a temperature of 30° C. to 200° C. and a pressure of 10 to 325 bar. In the second step, water or an alcohol having 1 to 20 carbon atoms is added at a temperature of 20° C. to 200° C. and a pressure of 1 to 325 bar. The catalyst is subsequently mechanically separated from the reaction medium.

KR19950013078B1 relates to a process for producing glycolic acid in which formaldehyde and carbon monoxide are reacted in the presence of water or water-methanol mixture using a heterogeneous solid catalyst, which is polymeric strong acid catalyst ion-exchanged by 5-40 wt % with monovalent metal of Group IB in a water-soluble inert solvent. Dioxane is used as a water-soluble inert solvent.

A similar process is described in KR19950013079B1 in which formaldehyde and carbon monoxide are reacted in the presence of water or water-methanol mixture using a polymeric strong acid catalyst in a water-soluble inert solvent.

A process for continuously manufacturing methyl glycolate from formaldehyde, carbon oxide and methanol is described in KR19950009480B1 in which a flow reactor filled with a polymeric strong acid catalyst is used. Reactant mixture of formaldehyde, water and inert solvent and carbon monoxide is supplied to the upper part of the reactor, and methanol is supplied to the lower part. In the upper part of the reactor, glycolic acid is produced via acid catalysis. In the lower part of the reactor, methyl glycolate is prepared from methanol and formed glycolic acid. The pressure of carbon monoxide is 500 to 6,000 psig and the temperature is 80 to 200° C. The suggested selectivity for this one-step procedure is relatively high.

KR0124821B1 relates to separating methylglycolate from an acidic solution. In this case, the reaction solution formed by a carbonylation reaction and an esterification reaction contains methyl glycolate, dioxane, water, methanol and hydrogen ion. This reaction solution is sent to a neutralization reactor and is neutralized by the addition of alkali to give a salt. The reaction solution containing salt is distilled to separate methanol, water and dioxane from methyl glycolate, salt and dioxane. The methanol separated from dioxane is recirculated to the carbonylation reactor. The solution which separated from the lower part of the distillation tower contains methyl glycolate, salt and dioxane. This is sent to a solid-liquid separator to separate the methyl glycolate from the solvent.

A further process for the production of methyl glycolate is described in KR19950011114B1. In this process formaldehyde is reacted with carbon monoxide to make a glycolic acid. The glycolic acid is then reacted with methanol to make a methyl glycolate. Residual formaldehyde is then reacted with methanol to make methylal. The methyl glycolate and methylal are then separated by distillation. The methylal is reacted with a Fe—Mo catalyst to return it to formaldehyde which is then recovered and concentrated before being recycled.

An alternative heterogeneous acid catalyst for the formaldehyde carbonylation reaction is described in U.S. Pat. No. 6,376,723. Sulfonic acid based ion exchange resins such as Amberlyst 38W and Nafion SAC13 are mentioned as suitable commercially available catalysts. Deloxan ASP 1/9, an alkyl sulfonic acid polysiloxane, is also listed as a suitable catalyst. This material is formed by co-polycondensation of propyl(3-sulfonic acid)siloxane and $SiO_2$.

He et al., Catalysis Today, 51 (1999), 127-134, discloses the use of heteropolyacids as homogeneous catalysts for the condensation of formaldehyde and methyl formate.

A further process is disclosed in JP2503178. In this process, glycolic acid is formed by hydrolysis of polyglycolide made from formaldehyde and carbon monoxide in the presence of a solid heteropoly acid.

WO2009/140787, WO2009/140788 and WO2009/140850 relate to processes using insoluble polyoxometalate compounds. These compounds either have specific acid properties or are encapsulated within zeolite cages, as solid acid catalysts, to produce glycolic acid from carbon monoxide and formaldehyde. However, the metal salts are prone to leaching of the metal component, which will reduce the number of active acid sites. In the case of zeolite impregnated with polyoxometalate salts, acid leaching will impact both the zeolite substrate and the salts themselves.

There are also a number of cases relating to various substituted organopolysiloxane compounds and their uses. These cases can be grouped into five families which cover different classes of polysiloxane compounds. The five groupings can be typified by: EP1360222, EP1786850, WO2006/013080, WO2007/090676 and US2010/0290962 which disclose various families of compounds. These documents suggest that the compounds may be useful for carbonylation reactions, but there is no detailed teaching as to how these compounds may be used in carbonylation reactions in general nor whether or how they may be used in the carbonylation of formaldehyde.

It has been suggested that the use of heterogeneous catalysts will reduce the corrosion of the reaction system. None of the heterogeneous catalysts proposed in the prior art has been adopted commercially.

Although there have been numerous patents and publications relating to the production of ethylene glycol from glycolic acid which is formed by carbonylation of formaldehyde, there remains a need for an improved process which can compete economically with the established industrial production route.

The various approaches to trying to solve the problems associated with the reaction can be summarised into two categories. The first relates to the investigation of homogeneous catalyst systems which operate at lower pressure and lower acid concentration than has previously been achievable.

The second relates to the investigation of heterogeneous solid acid catalysts as these benefit from easier separation of the catalyst and reduced reactor corrosion. However, the solid catalysts proposed to date have also proved to have a number of shortcomings and have not been adopted commercially. These catalysts generally lack the thermal and chemical stability required to withstand the severe reaction conditions.

For example, aluminosilicate zeolites are not stable under highly acidic conditions, as the aluminium is leached from the structure causing it to collapse. This results in loss of activity and eventually complete disintegration of the catalyst (Pan et al, 1994, Studies in Surface Science and Catalysis). With a view to avoid this problem, it is proposed in EP0114657 that the reaction should be operated such that the amount of acid formed is limited, but this reduces the efficiency of the reactor and exacerbates separation problems.

It is well known that sulfonic acid based ion exchange resins have limited thermal stability in aqueous environments leading to a loss of acid groups. Furthermore it has been found that formaldehyde attacks the aromatic rings within styrene/di vinyl benzene based resins causing swelling and further loss of acid groups.

It has been shown that substituted organopolysiloxane compounds, such as Deloxan ASP 1/9, Quadrasil—SA and Silicycle (SCX-2), and alkyl sulfonic acid polysiloxanes, can be used but these have been found to quickly lose catalytic performance at effective process conditions. This has been attributed to the loss of the tethered organic acid groups due to hydrolysis.

Processes for the production of ethylene glycol via the carbonylation of formaldehyde to glycolic acid which are economically viable are therefore sought.

In investigating the problem of solid acid catalyst stability in the formaldehyde carbonylation environment a large number of materials have been tested. In the course of this testing, it was observed that the initial activity of a functionalized catalytic silica material reduced with time. By 'functionalized', we mean that the silica material has acid groups, for example, alkyl sulfonic acid groups, tethered to the silica support. It has been discovered that the reduction in activity is a function of removal of the tethered functionalized groups.

An alternative catalyst and a process for the carbonylation of an aldehyde to form a carboxylic acid or derivate thereof is described in WO2016/162663. The catalyst disclosed therein comprises a homogeneous acid catalyst component and a porous solid component.

An alternative improved process for the production of glycolic acid is described in WO2016/162662. This process relates to the discovery that when the reaction is carried out in the presence of a small quantity of an homogeneous alkyl silyl sulfonic acid, that the reduction in activity of the silica material can be recovered or avoided. In some situations an enhanced activity can be achieved. Thus application no. WO2016/162662 relates to a process for the production of glycolic acid or derivatives thereof from formaldehyde comprising reacting formaldehyde with carbon monoxide and water in the presence of a silica catalyst, wherein from about 200 to about 1000 ppm of an alkyl silyl sulfonic acid is supplied to the reaction.

A still further process is described in GB application no 1615762.0. This process is for the production of a purified glycolic acid in which the glycolic acid produced by reacting formaldehyde with carbon monoxide and water in the presence of a sulfur catalyst is esterified using the catalyst of the carbonylation reaction to catalyse the esterification reaction, the sulfur catalyst is then removed from the alkylglycolate esterification by distillation and the alkylglycolate is then converted to the glycolic acid.

Whichever process is used for the production of glycolic acid, it may then be converted to ethylene glycol. This can be achieved by any suitable means. However, it is generally achieved by esterifying the glycolic acid with an alkanol, such as methanol, and subsequent hydrogenation to the ethylene glycol.

Various proposals for carrying out the glycolic acid esterification have been made. Where upstream processes include sulfur as a catalyst, the first step is generally the removal of the sulfur catalyst. One example of a process for producing the ester is described in U.S. Pat. No. 4,140,866. In this case the glycolic acid which has been prepared by the sulphuric acid catalysed carbonylation of formaldehyde is separated from the sulphuric acid by being contacted with an alkali metal hydroxide or carbonate, prior to esterification with an alkanol such as methanol.

Where the process for producing the glycolic acid is that described in GB application no 1615762.0 such that an esterification step is carried out in the presence of the carbonylation catalyst, the esterification product may be hydrogenated to form ethylene glycol rather than by being converted to glycolic acid or alternatively the glycolic acid produced by the process of GB application no 1615762.0 can be subsequently hydrogenated to form the ethylene glycol. In either event the catalyst carried over for the esterification may be removed before downstream purification commences.

Generally once the ester is formed, it will be hydrogenated to form the ethylene glycol. Again there have been several proposals made relating to this stage in the reaction. The majority of the proposals have related to the selection of catalyst for the hydrogenation. In one arrangement, a heterogeneous catalyst may be used. Heterogeneous catalysts which have been suggested include mixed oxides of copper and one or more of magnesium, manganese, nickel, iron, cobalt, chromium, calcium, barium, strontium, potassium, caesium, zinc, cadmium and silver and those described in U.S. Pat. Nos. 4,283,581, 4,366,333, 7,709,689, WO2012/024253, U.S. Pat. No. 7,538,060 and WO2008/100389.

The hydrogenation can also be carried out in the presence of a homogeneous catalyst. One example of a homogeneous hydrogenation system is described in U.S. Pat. No. 7,709,689 which is incorporated herein by reference. In this process, the catalyst comprises ruthenium, rhodium, iron, osmium, or palladium, and an organic phosphine. In this process at least 1% by weight water may be present during the hydrogenation.

A further process in which a homogeneous catalyst is used for the hydrogenation of glycolic acid and glycolic acid derivatives is described in U.S. Pat. No. 7,615,671 in which a ruthenium catalyst, a trivalent phosphorous compound and a promoter are used.

Alternatively, the ethylene glycol can be produced directly from the glycolic acid by hydrogenation. The hydrogenation can be vapour phase hydrogenation, liquid phase hydrogenation which may be fixed bed or slurry, or it may be homogeneous hydrogenation.

Whilst the various processes enable ethylene glycol to be produced, the product formed whilst being acceptable for some end uses does not reach the high purity specification required for other uses such as for use in the production of polyethylene terephthalate.

The Chinese National Standard GB/T 4649/2008 Super-grade specification and that of ASTM E2470-09 specification are detailed in Table 1.

TABLE 1

| Item | Unit | GB/T | ASTM |
|---|---|---|---|
| Ethylene glycol | wt % | 99.8 min | 99.9 min |
| Diethylene glycol | wt % | 0.1 max | 0.05 max |
| Acidity (as acetic acid) | wt ppm | 10 max | 20 max |
| Water | wt % | 0.1 max | 0.05 max |
| Colour (Pt—Co) before heating | | 5 max | 5 max |
| After heating with HCl | | 20 max | |
| Density (at 25° C.) | g/cm$^3$ | 1.1128-1.1138 | 1.1129-1.1134 |
| Boiling range | ° C. | 196-199 | 196-200 |
| Aldehyde (as formaldehyde) | wt ppm | 8 max | |
| Aldehyde (as acetaldehyde) | wt ppm | | 10 max |
| Iron | wt ppm | 0.1 max | 0.1 max |
| Ash content | wt ppm | 10 max | 40 max |
| Chlorides (as Cl) | wt ppm | 0.5 max | 0.2 max |
| Ultraviolet Transmittance | % | | |
| 200 nm | | 75 | 70 |
| 250 nm | | | 90 |
| 275 nm | | 92 | 94 |
| 350 nm | | 99 | 98 |

The UV transmittance requirement detailed in Table 1 is particularly problematic and prior art processes do not provide products which meet this requirement. Without wishing to be bound by any theory, it is believed that the measure of UV transmittance is sensitive to trace contamination of the ethylene glycol product with glycolate esters.

Other key impurities in ethylene glycol are 1,2-propylene glycol and 1,2-butylene glycol. These impurities are generated in low level amounts during the hydrogenation process. Unfortunately, they cannot readily be separated from ethylene glycol by distillation. Since the analytical techniques used in the standards detailed above, are not able to quantify the amount of these components present, they are not separately identified and therefore will be included in the amount of ethylene glycol identified as being present. However their presence will reduce the quality of product achieved in downstream processes.

Whichever method is used to produce the ethylene glycol, problems have been encountered associated with the purification of the product. For example, where unhydrogenated ester is carried forward in the stream of ethylene glycol this can lead to excessive residence time or concentrations in the separation column which in turn can lead to the formation of compounds which serve as UV inhibitors thereby making it impossible to meet the UV specification required for some end uses, such as for use on the formation of clear plastic bottles and the like. In addition, compounds which are UV inhibitors may be present in the stream recovered from the hydrogenation reaction and it can be difficult to separate these from the desired ethylene glycol.

A further problem relates to the presence of diethylene glycol in the product stream removed from the hydrogenation reaction. This too can be difficult to separate from the ethylene glycol. Even more problematic is the separation of compounds which have a volatility between that of ethylene glycol and diethylene glycol. One such compound is the ethylene glycol ester of alkoxyacetic acid such as methoxyacetic acid. In view of the number of potential reactions which could be carried out either in the hydrogenation or during the separation itself, it is likely that other difficult to separate components will be formed. Although they may only be present in small quantities, their presence will reduce the quality of the product and so it is desirable that they be separated.

In addition to the removal of the ester of the alkoxyacetic acid being problematic, the presence of alkoxyacetic acid, such as methoxyacetic acid, is problematic since it is difficult to separate from the ethylene glycol as they are close boilers and may form an azeotrope. Further, as detailed above, it may esterify with the ethylene glycol.

Another component which may be present where there has been an upstream esterification and which may form an azeotrope with ethylene glycol making its separation problematic is dimethyl diglycolate. Similar problems may be noted with other dialkyl diglycolate. In this connection it will be understood that that a dialkyl diglycolate is the dialkyl ester of diglycolic acid. Similarly dimethyl diglycolate is the dimethyl ester of diglycolic acid.

It is therefore desirable to provide a process for the purification of ethylene glycol howsoever formed which reduces and preferably solves one or more of the problems associated with prior art processes. It is particularly desirable to provide a process which enables an ethylene glycol product to be achieved which meets and preferably exceeds the standards of product required.

Thus, according to a first aspect of the present invention, there is provided a process for the purification of ethylene glycol from a crude stream thereof, the process comprising:
(a) passing the stream of crude ethylene glycol to a first distillation column in which light compounds within the crude stream are separated overhead and a lights-removed crude ethylene glycol stream is removed from at or near the bottom of the first distillation column;
(b) passing the lights-removed crude ethylene glycol stream removed from at or near the bottom of the first distillation column to a second distillation column in which purified ethylene glycol is separated and recovered from heavy components present in the lights-removed crude ethylene glycol stream;
(c) removing a stream from at or near the bottom of the second distillation column which comprises residual ethylene glycol together with diethylene glycol and heavy compounds and passing said stream to a third distillation column in which the heavy compounds are separated from the stream comprising ethylene glycol and diethylene glycol;
(d) removing the stream comprising ethylene glycol and diethylene glycol from the third distillation column and passing said stream to a fourth distillation column in which the ethylene glycol is separated from the diethylene glycol.

Where the ethylene glycol has been formed by esterification of glycolic acid and subsequent hydrogenation, the crude ethylene glycol stream will generally first be treated in an alkanol distillation column in which water and alkanol will be removed before the crude stream is passed to the first distillation column in step (a).

By the process of the present invention at least some of the problems associated with the prior art process are addressed and preferably overcome.

The alkanol distillation column may be of any suitable configuration. In general it will be a packed column. It may be operated at any suitable conditions provided that it allows the water and alkanol to be separated from the ethylene glycol stream. In general, it will be operated at a pressure below atmospheric pressure. In one arrangement it may be operated at a pressure at the column top of about 20 kPa to about 40 kPa or at about 30 kPa. The alkanol distillation column may be operated at any suitable pressures, suitable pressures include those of about 155° C. to about 175° C. or about 165° C.

The water and alkanol separated from the ethylene glycol may be recycled to upstream reactions. Where upstream reactions include esterification, the recycle may be to the esterification reactor. The water may be separated from the alkanol before the alkanol is returned to the esterification reactor. Where the esterification has been carried out with methanol it is methanol, or methanol and water which will be recycled to the esterification reactor.

Any 2-alkoxyethanol present in the stream passed to the alkanol distillation column is removed from the ethylene glycol stream with the alkanol such as methanol and/or water stream and is thereby separated from any alkyl glycolate present in the crude ethylene glycol stream. This is a particular advantage of the present invention. The alkyl glycolate will be passed in the ethylene glycol stream to the first distillation column. Where the esterification has been carried out with methanol, water/2-methoxy ethanol is separated from any methyl glycolate which is present in the crude ethylene glycol stream and the water/2-methoxy ethanol is passed in that stream to the first distillation column.

The first distillation column may be of any suitable configuration. In general it will be a packed column. It may be operated at any suitable conditions provided that it allows light components present in the stream to be separated from the stream comprising the ethylene glycol stream. In this connection, it will be understood that "light" components are those which have a lower boiling point than ethylene glycol and therefore will be separated from the ethylene glycol stream and removed from at or near the top of the column.

In general, the first distillation column may be operated at a pressure below atmospheric pressure. In one arrangement it may be operated at a pressure at the column top of from about 10 kPa to about 20 kPa or at about 15 kPa. The temperature in the bottom of the column may be from about 140° C. to about 160° C., or about 145° C. to about 150° C. or about 147° C.

In this first distillation column lights will be separated from the ethylene glycol. Where the ethylene glycol has been formed by esterification followed by hydrogenation, the lights may comprise one or both of alkyl glycolate, 2-hydroxyalkyl-1,3-dioxolane. Where methanol has been used in the esterification process, the lights may comprise one or both of methyl glycolate and, 2-hydroxymethyl-1,3-dioxolane. The lights may also include, for example, 1,2-propylene glycol and/or 1,2-butylene glycol. These light intermediates will be removed from at or near the top of the column. A particular advantage of the process is the ability to remove the lights such as the dioxolane at the low pressure. Where the alkyl species used to form the alkyl glycolate is sufficiently large, the alkyl glycolate will not be part of the lights stream removed.

In order to ensure complete separation of the light components, some ethylene glycol can be allowed to pass overhead. The stream of light components removed may be recycled to upstream processes. In one arrangement, it may be recycled to the hydrogenation reaction. Since the light stream removed is recycled, any ethylene glycol removed in the stream is not lost from the overall process and thus the economics of the system are not compromised.

The crude ethylene glycol stream having a higher concentration of ethylene glycol than the stream fed to the first distillation column that is recovered from at or near the bottom of the first distillation column is passed to the second distillation column.

The second distillation column can be of any suitable configuration. In general it will be a packed column. It may be operated at any suitable conditions provided that it allows the ethylene glycol to be separated from heavy components including diethylene glycol and ethylene glycol glycolate. It will be understood that "heavy" components are those having a higher boiling point that that of ethylene glycol.

In general, the second distillation column may be operated at a pressure below atmospheric pressure. In one arrangement it may be operated at a pressure of from about 6 kPa to about 10 kPa or at about 8 kPa at the column top. The temperature in the bottom of the column may be from about 140° C. to about 160° C., or about 145° C. to about 150° C. The pressure at the columns bottom may be from about 8 kPa to about 11 kPa or about 9 kPa to about 10 kPa.

The ethylene glycol will generally be recovered as a side draw. The side draw will be taken from any suitable point but will generally be removed at a point above the point at which the stream from the first distillation column was fed to the second distillation column.

To facilitate a clean separation of ethylene glycol from the heavy components without compromising the operability of the second distillation column, a minor portion of the ethylene glycol is allowed to slip into the stream recovered from at or near the bottom of the second distillation column comprising the diethylene glycol and ester compounds.

Any suitable amount of ethylene glycol may be allowed to slip into the stream recovered from at or near the bottom of the second distillation column comprising the diethylene glycol and ester compounds provided that it is a minor amount.

The bottom stream from the second distillation column which comprises some ethylene glycol, the diethylene glycol and ester compounds are passed to the third distillation column. In one arrangement about 2% to about 5%, or about 3% to about 4%, of the monoethylene glycol may be allowed to slip into the column bottoms.

The third distillation column can be of any suitable configuration. In general it will be a packed column. It may be operated at any suitable conditions provided that it allows the ethylene glycol heavy ester compounds to be separated from the diethylene glycol and the remaining ethylene glycol.

In general, the third distillation column may be operated at a pressure below atmospheric pressure. In one arrangement it may be operated at from about 2 kPa to about 8 kPa or at about 3 kPa to about 6 kPa or about 4 kPa at the column top.

The heavy ester compounds will be removed from at or near the bottom of the third distillation column. The ester compounds removed in this stream may be one or more of ethylene glycol glycolate, the esterification product of alkyl glycolate, usually monoethylene glycolate, and glycolic acid. In a preferred arrangement, the third distillation column will be operated such that the stream removed from at or near the top of the column, which will comprise the ethylene glycol and diethylene glycol will be essentially free of ester compounds.

The stream recovered from at or near the bottom of the third distillation column which will include the ester components and any other heavy by-products can be recycled to the upstream hydrogenation reactor where further ethylene glycol can be formed and thus the removal of the heavy products will not represent a loss of product to the system. However, a purge will generally be taken from the recycle stream to prevent a build up of heavies in the system.

The stream comprising ethylene glycol and diethylene glycol is passed to the fourth distillation column. The fourth distillation column can be of any suitable configuration. It will generally be a packed column. It may be operated at any suitable conditions provided that it allows the ethylene glycol to be separated from the diethylene glycol.

In general, the fourth distillation column may be operated at a pressure below atmospheric pressure. In one arrangement it may be operated at about 2 kPa to about 4 kPa or at about 3 kPa at the column top. Bottom temperatures of about 150° C. to about 175° C. may be appropriate.

The diethylene glycol, which is itself a useful product, is removed from at or near the bottom of the fourth distillation column. The ethylene glycol which was allowed to slip from the second distillation column is removed from the fourth distillation column from a stream recovered from at or near the top thereof. It may be recovered or it may be returned to the second separation column.

By the use of the train of distillation columns of the present invention, particularly when operated at vacuum, enable the desired separation to be carried out and high purity ethylene glycol to be produced. It also enables diethylene glycol, a useful by-product, to be separated. The process enables the risk of trans-esterification reactions occurring during separation which was a problem with prior art processes to be overcome.

In an alternative arrangement, the third distillation column may be configured to separate monoalkyleneglycolate and other components that are lighter than diethyleneglycol overhead. In this arrangement the stream recovered may be recycled to the second distillation column such that the monoethyleneglycol can be recovered.

Components having a volatility between that of monoethylene glycol and diethylene glycol may accumulate in the loop between the second and third columns and thus a purge may be taken. These components may be methoxyacetic acid and ethylene glycol-methoxyacetate. The purge may be returned to the hydrogenation.

In this arrangement, the fourth column will separate the diethyleneglycol in a side draw above the feed of heavy esters in the column bottoms. In this arrangement, the bottoms stream may be recycled to the hydrogenation with a purge being taken to control accumulation of any heavies which are not hydrogenated. The overhead stream form the fourth column will contain diethyleneglycol and any lights such as monoethyleneglycol and water that are formed from reactions in this column. The overhead stream recycled to the second column to recover monoethylene glycol, with a purge to hydrogenation to control potential accumulation of components in this recycle loop.

With the process of the present invention, monoethylene glycol of high purity can be achieved. Purities in the region of 99.9% or above may be achieved.

The process will now be described by way of example with reference to the accompanying drawing in which.

It will be understood by those skilled in the art that the drawings are diagrammatic and that further items of equipment such as reflux drums, pumps, vacuum pumps, compressors, gas recycle compressors, temperature sensors, pressure sensors, pressure relief valves, control valves, flow controllers, level controllers, and the like may be required in a commercial plant. The provision of such ancillary items of equipment forms no part of the present invention and is in accordance with conventional chemical engineering practice.

Figure 1:
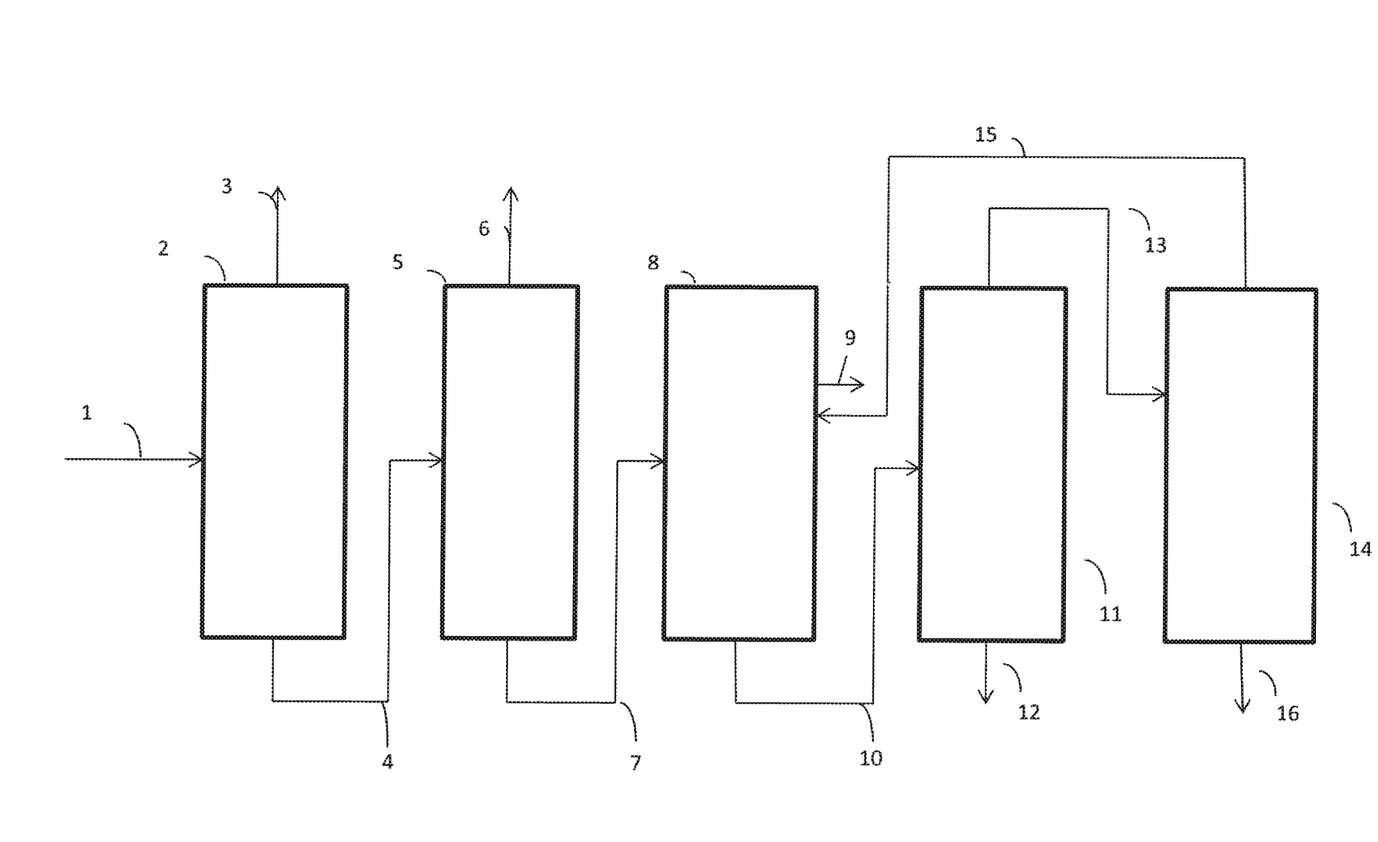
FIG. 1 is a schematic representation of one arrangement of the present invention.

The process will be discussed in connection with a process in which the ethylene glycol has been formed by esterification of glycolic acid with methanol with subsequent hydrogenation. However, it will be understood that it can be equally appropriate for the purification of ethylene glycol formed by alternative processes.

Where there has been an esterification and hydrogenation, the crude ethylene glycol stream will be passed in line 1 to the alkanol distillation column 2 where alkanol such as methanol and water are removed in line 3 from at or near the top of the alkanol distillation column. Thus may be recycled to upstream processes.

The remaining crude ethylene glycol stream is removed from at or near the bottom of the alkanol distillation column and passed in line 4 to the first distillation column 5. Where there is no requirement for the alkanol distillation column, such as where the ethylene glycol has been provided by a process other than one requiring esterification followed by hydrogenation, the ethylene glycol will be passed directly to the first distillation column 5.

Lights separated from the ethylene glycol will be removed from at or near the top of the first distillation column 5 in line 6. Some ethylene glycol may be allowed to slip into this stream to ensure complete separation.

The lights reduced ethylene glycol stream is removed from at or near the bottom of distillation column 5 and passed in line 7 to the second distillation column 8 where the ethylene glycol is separated from the heavy components. The purified ethylene glycol is recovered from the second distillation column 8. This will generally be taken as a side draw in line 9. An overhead stream may be removed. This may contain monoethylene glycol and small quantities of water and other lights that will be formed from the reactions in the column.

This overhead stream, where present may be passed to an alkanol separation column to separate the water and so that the monoethylene glycol can be recovered.

A stream 10 will be recovered from at or near the bottom of the second distillation column 8 comprising residual ethylene glycol together with diethylene glycol and heavy compounds will be passed to the third distillation column 11. In the third distillation column 11, the heavy compounds, such as esters, will be separated and removed form at or near the bottom of the column in line 12. The ethylene glycol and the diethylene glycol are removed from at or near the top of the third distillation column 11 in line 13 and passed to the fourth distillation column 14 where the ethylene glycol and diethylene glycol are separated. The ethylene glycol is recovered from at or near the top of the fourth distillation column 14 in line 15. It may be recovered directly or it may be recycled to the second distillation column 8. The diethylene glycol will be recovered in line 16 from at or near the bottom of the fourth distillation column 14.

The present invention will now be described with reference to the following examples.

EXAMPLE 1

The process of the present invention was investigated using a series of three 1 inch diameter pilot columns, connected in series. A crude monoethylene glycol stream is formed by a series of reactions comprising hydrocarbonylation of formaldehyde, esterification of the product glycolic acid with methanol, and the homogeneous hydrogenation of the glycolic acid ester.

This crude stream is fed to a low boiler column, with top and bottom streams being recovered. The bottom stream is then passed to a crude monoethylene glycol column with top and bottom streams being recovered. The bottom stream is then passed to a monoethylene product column from which the monoethylene glycol is recovered as a side draw.

Operating conditions and results are set out in Table 1.

TABLE 1

| Low Boiler Column | | Crude MEG Lights Column | | MEG Product Column | | Summary |
|---|---|---|---|---|---|---|
| Feed Rate | 100 g/hr | Feed Rate | 63 g/hr | Feed Rate | 60 g/hr | Total monoethyleneglycol Recovery 90.2% |

TABLE 1-continued

| | Low Boiler Column | | Crude MEG Lights Column | | MEG Product Column | | Summary |
|---|---|---|---|---|---|---|---|
| Feed Temperature | 30 | C. | Feed Temperature | 80 C. | Feed Temperature | 80 C. | Monoethyleneglycol Purity 99.96 wt % |
| Bottoms Split | 63% | | Bottoms Split | 95% | Bottoms Split | 8% | |
| Reflux Ratio | 140 | g/hr | Reflux Ratio | 210 g/hr | Reflux Ratio | 400 g/hr | |
| Reflux Temperature | 33 | C. | Reflux Temperature | 125 C. | Reflux Temperature | 82 C. | |
| Pressure | 225 | mmHg | Pressure | 113 mmHg | Pressure | 68 mmHg | |

The typical concentrations found in the streams of the three columns are set out in Table 2.

TABLE 2

| | Feed | Overheads | Bottoms | Side Draw |
|---|---|---|---|---|
| Column 1 | | | | |
| Monoethylene glycol stream concentration wt % | 59.7 | 0.0 | 94.5 | Not present |
| Stream split % | 100 | 36.8 | 63.2 | Not present |
| Column 2 | | | | |
| Monoethylene glycol stream concentration wt % | 94.5 | 88.7 | 94.7 | Not present |
| Stream split % | 100 | 4.9 | 95.1 | Not present |
| Column 3 | | | | |
| Monoethylene glycol stream concentration wt % | 94.7 | 98.6 | 51.3 | 99.9 |
| Stream split % | 100 | 10 | 80 | 10 |

The invention claimed is:

1. A process for the purification of ethylene glycol from a crude stream thereof, the process comprising:
 (a) passing the stream of crude ethylene glycol to a first distillation column in which light compounds within the crude stream are separated overhead and a lights-removed crude ethylene glycol stream is removed from at or near the bottom of the first distillation column;
 (b) passing the lights-removed crude ethylene glycol stream removed from at or near the bottom of the first distillation column to a second distillation column in which purified ethylene glycol is separated and recovered from heavy components present in the lights-removed crude ethylene glycol stream; and,
 (c) performing steps (c1) and (c2):
  (c1) removing a stream from at or near the bottom of the second distillation column which comprises residual ethylene glycol together with diethylene glycol and heavy compounds and passing said stream to a third distillation column in which the heavy compounds are separated from the stream comprising ethylene glycol and diethylene glycol; and,
  (c2) removing the stream comprising ethylene glycol and diethylene glycol from the third distillation column and passing said stream to a fourth distillation column in which the ethylene glycol is separated from the diethylene glycol,
 or, performing steps (c3) and (c4):
  (c3) removing a stream from at or near the bottom of the second distillation column which comprises residual ethylene glycol together with diethylene glycol and heavy compounds and passing said stream to a third distillation column in which components that are lighter than diethylene glycol are separated in an overhead stream; and,
  (c4) removing a stream comprising diethylene glycol from the third distillation column and passing said stream as a feed to a fourth distillation column in which a diethylene glycol stream is separated in a side draw.

2. The process according to claim 1 wherein the crude ethylene glycol stream is first treated in an alkanol distillation column in which water and alkanol will be removed before the crude stream is passed to the first distillation column in step (a).

3. The process according to claim 1 wherein each distillation column is operated a pressure below atmospheric pressure.

4. The process according to claim 2 wherein the alkanol distillation column is operated at a pressure at the column top of about 20 kPa to about 40 kPa or at about 30 kPa.

5. The process according to claim 1 wherein the first distillation column is operated at a pressure at the column top of from about 10 kPa to about 20 kPa or at about 15 kPa.

6. The process according to claim 1 wherein the second distillation column is operated at a pressure of from about 6 kPa to about 10 kPa or at about 8 kPa at the column top.

7. The process according to claim 1 wherein when steps (c1) and (c2) are performed, the third distillation column is operated at a pressure of from about 4 kPa to about 8 kPa or at about 6 kPa at the column top.

8. The process according to claim 1 wherein when steps (e1) and (c2) are performed, the fourth distillation column is operated at from about 2 kPa to about 4 kPa or at about 3 kPa at the column top.

9. The process according to claim 1, wherein when steps (c3) and (c4) are performed, the overhead stream from the third distillation column is recycled to the second distillation column.

10. The process according to claim 9, wherein a purge is taken from the recycled overhead stream from the third distillation column.

11. The process according to claim 10, wherein the purge is returned to an upstream hydrogenation to produce ethylene glycol.

12. The process according to claim 1, wherein when steps (c3) and (c4) are performed, a bottoms stream is recycled from the fourth distillation column to an upstream hydrogenation.

13. The process according to claim 12, wherein a purge is taken from the bottoms stream to control accumulation of any heavies which are not hydrogenated.

14. The process according to claim 1, wherein when steps (c3) and (c4) are performed, an overhead stream is withdrawn from the fourth distillation column containing diethylene glycol and any lights that are formed from reactions in the fourth distillation column.

15. The process according to claim 14, wherein the overhead stream from the fourth distillation column is recycled to the second distillation column.

16. The process according to claim 15 wherein a purge to an upstream hydrogenation is taken from the overhead stream from the fourth distillation column.

17. The process according to claim 14, wherein the lights comprise monoethylene glycol, water, or both.

* * * * *